US008252753B2

(12) United States Patent
Kurfurst et al.

(10) Patent No.: US 8,252,753 B2
(45) Date of Patent: Aug. 28, 2012

(54) OLIGONUCLEOTIDE AND THE USE THEREOF FOR MODULATING AN ISOFORM C BETA-1 PROTEIN-KINASE IN THE FORM OF A SKIN DEPIGMENTATION AGENT

(75) Inventors: Robin Kurfurst, Olivet (FR); Carine Nizard, Ivry sur Seine (FR)

(73) Assignee: L V M H Recherche, Saint Jean de Braye (FR)

( * ) Notice: Subject to any disclaimer, the term of this patent is extended or adjusted under 35 U.S.C. 154(b) by 0 days.

(21) Appl. No.: 10/584,982

(22) PCT Filed: Dec. 28, 2004

(86) PCT No.: PCT/FR2004/003397
§ 371 (c)(1),
(2), (4) Date: Apr. 2, 2007

(87) PCT Pub. No.: WO2005/073243
PCT Pub. Date: Aug. 11, 2005

(65) Prior Publication Data
US 2007/0274936 A1 Nov. 29, 2007

(30) Foreign Application Priority Data

Dec. 30, 2003 (FR) ..................... 03 15560

(51) Int. Cl.
*A61K 31/70* (2006.01)
*C07H 21/02* (2006.01)
*C07H 21/04* (2006.01)

(52) U.S. Cl. .................. 514/44 A; 536/24.1; 536/24.5

(58) Field of Classification Search .............. 514/44; 435/6, 91.1, 325, 375; 536/23.1, 24.3, 24.33, 536/24.5
See application file for complete search history.

(56) References Cited

U.S. PATENT DOCUMENTS 4,621,023 A 11/1986 Redziniak et al.
6,365,135 B1 4/2002 Philippe et al.

FOREIGN PATENT DOCUMENTS

| DE | 198 06 947 A1 | 8/1999 |
|---|---|---|
| WO | WO-95/02069 A1 | 1/1995 |
| WO | WO-97/35998 A1 | 10/1997 |
| WO | WO-99/22707 A1 | 5/1999 |
| WO | WO-99/24035 A1 | 5/1999 |
| WO | WO-99/25819 A2 | 5/1999 |
| WO | WO-01/58918 A2 | 8/2001 |

OTHER PUBLICATIONS

Lazou et al. The use of antisense strategy to modulate human melanogenesis. Journal of Drugs in Dermatology, 2007 vol. 6:s2-27.*
Brand, RM. (Curr Opin Mol Ther. Jun. 2001;3(3):244-8).*
Nishizuka, Y., "The molecular heterogeneity of protein kinase C and its implications for cellular regulation," Nature, vol. 334, Aug. 25, 1988, pp. 661-665.
Park, H.Y., et al., "The Beta Isoforrn of Protein Kinase C Stimulates Human Melanogenesis by Activating Tyrosinase in Pigment Cells," The Journal of Biological Chemistry, vol. 268, No. 16, Jun. 5, 1993, pp. 11742-11749.
Jacubovich, R., et al., "Tumour-associated Antigens in Culture Medium of Malignant Melanoma Cell Strains," Cancer Immunology and Immunotherapy, vol. 7, 1979, pp. 59-64.
Ohno, S. et al., "Protein kinase C, beta type (EC 2.7.1.-) (PKC-beta) (PKC-B)," SWISS-PROT, Nov. 1, 1988, 2 pages.
Hug, et al., "Protein kinase C isoenzymes: divergence in signal transduction?" Biochem. J., 1993, pp. 329-343, vol. 291.
Kubo, K., et al., "Primary structures of human protein kinase C βI and βII differ only in their C-terminal sequences," FEBS Letters, vol. 223, No. 1 (Oct. 1987) pp. 138-142.
Cejas, P.J., et al., "Protein Kinase C βII Plays an Essential Role in Dendritic Cell Differentiation and Autoregulates Its Own Expression," The Journal of Biological Chemistry, vol. 280, No. 31 (Aug. 5, 2005) pp. 28412-28423.

* cited by examiner

*Primary Examiner* — Terra Cotta Gibbs
(74) *Attorney, Agent, or Firm* — Blakely, Sokoloff, Taylor & Zafman

(57) ABSTRACT

This invention relates to oligonucleotide sequences and their derivatives.
These oligonucleotide sequences are capable of hybridising with the genes or with products of the genes coding for the PKC-beta 1.
This invention also relates to the use of these oligonucleotide sequences as a depigmenting or bleaching agent for the skin in a cosmetic composition or in a topical pharmaceutical composition.

20 Claims, No Drawings

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial sequence
<220> FEATURE:
<223> OTHER INFORMATION: Oligonucleotide

<400> SEQUENCE: 1
acaccccagg ctcaacgatg                                                  20

<210> SEQ ID NO 2
<211> LENGTH: 20
<212> TYPE: DNA
<213> ORGANISM: Artificial sequence
<220> FEATURE:
<223> OTHER INFORMATION: Oligonucleotide

<400> SEQUENCE: 2
tggagtttgc attcacctac                                                  20

<210> SEQ ID NO 3
<211> LENGTH: 20
<212> TYPE: DNA
<213> ORGANISM: Artificial sequence
<220> FEATURE:
<223> OTHER INFORMATION: Oligonucleotide

<400> SEQUENCE: 3
aaaggcctct aagacaagct                                                  20

<210> SEQ ID NO 4
<211> LENGTH: 20
<212> TYPE: DNA
<213> ORGANISM: Artificial sequence
<220> FEATURE:
<223> OTHER INFORMATION: Oligonucleotide

<400> SEQUENCE: 4
gccagcatct gcaccgtgaa                                                  20
```

```
<210> SEQ ID NO 5
<211> LENGTH: 20
<212> TYPE: DNA
<213> ORGANISM: Artificial sequence
<220> FEATURE:
<223> OTHER INFORMATION: Oligonucleotide

<400> SEQUENCE: 5
ccgaagctta ctcacaattt                                              20
```

OLIGONUCLEOTIDE AND THE USE THEREOF FOR MODULATING AN ISOFORM C BETA-1 PROTEIN-KINASE IN THE FORM OF A SKIN DEPIGMENTATION AGENT

This is a non-provisional application claiming the benefit of International application number PCT/FR2004/003397 filed Dec. 28, 2004.

This invention relates to oligonucleotide sequences and their derivatives capable of hybridising with the gene or with products of the gene coding for the beta-1 isoform of Protein-Kinase C(PKC) (PKC-beta-1).

This invention also relates to the use of these new oligonucleotide sequences as a depigmenting or bleaching agent for the skin in a cosmetic composition or in a dermatological composition.

In man, pigmentation is the result of synthesis and distribution of melanin pigments in the skin, hair follicles or eyes. Pigmentation is genetically predefined but it is regulated by many internal or external factors. The colour of human skin will be determined by melanins produced by melanocytes and the number of melanocytes, their tyrosinasic activity and their capability of exporting melanins to keratinocytes, and the size of melanosomes that contain melanin grains. For each individual, the colour of the skin varies mainly depending on the degree of irradiation with ultraviolet (UV) rays. In other words, for each individual, there is a basic skin pigmentation when he or she is subjected to a minimum amount of UV irradiation corresponding to his or her lightest skin colour, and a more intense skin pigmentation corresponding to stronger UV irradiation, until a maximum pigmentation corresponding to his or her darkest skin colour after exposure to intense UV irradiation, like that encountered at high altitude in the mountains, for a long period.

Furthermore, as is well known, there is a very great genetic diversity in the world population in terms of skin pigmentation. Thus, depending on the population, the colour of the skin corresponding to the basic pigmentation defined above may be lighter or darker, varying between the two extremes of very light and very dark. The difference in skin colour between the basic pigmentation and the maximum pigmentation is also variable, depending on the population. Thus, it is well known that persons belonging to some populations with light skin (basic pigmentation) react quickly and/or severely to the action of UV irradiation and can therefore easily have a darker tan, even when these persons have not been deliberately exposed to the sun for a long period. In the remainder of this description, such persons will be referred to by the expression "persons very reactive to UV irradiation". This is particularly true of persons originating from Asia or some so-called mixed populations.

Furthermore, some persons will develop areas and/or spots that are darker and/or more coloured making the skin look non-uniform, particularly on their face or hands. These spots are due to a high concentration of melanin in the keratinocytes in the epidermis.

The mechanism for the formation of skin pigmentation involves the synthesis of melanins. This mechanism is particularly complex and diagrammatically involves the following main steps:

Tyrosine→Dopa→Dopaquinone→Dopachrome→Melanins

Tyrosinase, activated by a phosphorylation reaction catalysed by Protein Kinase C, is an essential enzyme acting in this sequence of reactions. In particular, tyrosinase catalyses the transformation reaction of tyrosine into Dopa (Dihydroxyphenylalanine) and the transformation reaction of Dopa into Dopaquinone leading to the formation of melanin pigments.

A molecule is recognised as being depigmenting when it acts directly on epidermal melanocytes by inhibiting the activity of these cells and/or if it blocks one of the steps in the biosynthesis of melanins. This is the case particularly when the molecule inhibits one of the enzymes involved in melanogenesis, or when it reacts with chemical compounds in the melanin synthesis sequence.

Known depigmenting substances include particularly hydroquinone and its derivatives, ascorbic acid and its derivatives, placentary extracts, kojic acid, arbutin, iminophenols (WO 99/22707), association of carnitin and quinone (DE 19806947), amide derivatives of amino-phenol (FR 2 772 607), and derivatives of benzothiazole (WO 99/24035). These substances may have some disadvantages. They may be unstable, require use at high concentrations, they may lack specificity in their action mode, or they may have a cytotoxic capability or be irritant.

Topical use of efficient and inoffensive depigmenting substances is required particularly in cosmetics and dermatology. These substances are used in particular to treat regional hyper pigmentation due to melanocyte hyper-activity such as idiopathic melasma, local hyper pigmentation due to hyper-activity and mild melanocyte proliferation such as pigmentary spots called age spots (senile lentigos), accidental hyper pigmentation such as photosensitization or post-lesion healing, and some leucodermies such as vitiligo. In the latter cases, instead of repigmenting the skin, the pigmentation around the periphery of the depigmented areas is attenuated so that the skin becomes more uniform in colour.

Depigmenting substances are also used by some persons as skin bleaching agents, particularly persons mentioned above who are very reactive to UV rays, to lighten their colour particularly on their face and hands, so as to keep the skin colour as light as possible or at least to reduce the pigmenting effects of UV rays.

The problem therefore that arises for professionals is the design, fabrication or isolation of new depigmenting substances or new bleaching agents for the human skin or hair, without the disadvantages of known substances, in other words that are not irritating, non-toxic, and/or non-allergenic for the skin, that have a stable composition and are active at a very low concentration with no cytotoxicity.

The use of an antisense oligonucleotide to treat diseases caused by a malfunction of the melanocytes, and particularly vitiligo and other depigmenting diseases, has been described in WO 99/25819. Hypo pigmentation in these cutaneous pathologies is the result of an abnormally high content of tenascine. The oligonucleotides described in this document act against hypo pigmentation by regulating the expression of tenascine.

On the other hand, the subject of this invention is to provide a depigmenting agent acting on the melanogenesis process intended firstly, in the case of an approximately uniform pigmentation, for bleaching the skin or hair, in other words to reduce their pigmentation and secondly to reduce skin hyper pigmentation, namely when the skin pigmentation is non-uniform.

Patent application WO 01/58918 describes oligonucleotides capable of specifically hybridising with the gene or a product of the gene coding for tyrosinase or tyrosinase related-protein 1, which are enzymes used in the metabolism of melanin. The described sequences can be used to develop compositions acting as a depigmenting or bleaching agent for the skin or hair.

The inventors of this invention found that surprisingly, oligonucleotide sequences other than those that can specifically hybridise with enzymes specifically involved in the metabolism of melanin, were useful and efficient as a depigmenting or bleaching agent for the skin or hair, without any side effects.

The purpose of this invention is an oligonucleotide with between 7 and 25 nucleotides, preferably 20, capable of specifically hybridising with genes or products of genes coding for protein kinase C beta-1 (PKC beta-1).

The inventors of this invention found that oligonucleotides capable of specifically hybridising with the gene or products of the genes (such as RNAs) coding for the PKC beta-1 isoform have a depigmenting activity. This activity exists even at a very low concentration, which increases the usefulness of these oligonucleotides. Furthermore, these oligonucleotides according to the invention are not cytotoxic.

Oligonucleotides according to the invention are involved on the input side of melanogenesis mechanisms by modulating the expression of PKC beta-1 and therefore its activity. Consequently, the reduction in the activity of PKC beta-1 leads to a reduction in the phosphorylation of tyronisase in melanocytes.

Oligonucleotides according to the invention provide an ideal solution to the problems that arise with conventionally used substances. Known substances that inhibit the activity of tyrosinase (particularly hydroquinone and its derivatives, ascorbic acid and its derivatives, placentary extracts, kojic acid, arbutin) have many side effects that are unacceptable due to their low specificity.

Therefore, this invention solves the problems encountered in prior research work by modulating the activation of the enzyme by phosphorylation instead of directly inhibiting the enzyme after it has been activated to obtain the depigmenting effect.

The term "oligonucleotide" as used in this invention means polynucleotides formed from natural nucleobases and pentafuranosyl groups (sugar) forming nucleosides that are connected together by native phosphodiester links. Therefore the term "oligonucleotides" refers to natural species or to synthetic species formed from natural sub-units or near homologues of them.

The term "oligonucleotides" denotes a structure comprising nucleotides, preferably deoxyribonucleotides, but also ribonucleotides. The term concerns only the primary structure of the molecule. Thus, this term includes double or single strand DNA, and double or single strand RNA.

The term "oligonucleotides" can also refer to parts that perform functions similar to functions of natural oligonucleotides but that may have unnatural portions. Oligonucleotides may have sugar parts, nucleobase parts or modified internucleotide links. The preferred modifications among the possible modifications are 2'-O-alkyl derivatives on the sugar part, particularly 2'-O-ethyloxymethyl or 2'-O-methyl, and/or phosphorothioates or methylphosphonates for the internucleotide skeleton.

Chimeric oligonucleotides are included in the preferred modifications of the invention. Oligonucleotides contain at least two chemically different regions, each comprising at least one nucleotide. In particular, they consist of one or several regions comprising a modified nucleotide that confers one or more beneficial properties, for example such as better biological stability, increased bioavailability, increased cellular internalisation or an increase in the affinity for the target RNA.

Preferably, the internucleotide skeleton may consist in whole or in part of phosphodiesters, or phosphorothioates, or methylphosphonates or combinations of phosphodiester and/or phosphorothioate and/or methylphosphonate links.

The term "oligonucleotide" can also refer to oligonucleotides to which a plasmidic type circular administration vector or a nucleic or peptidic acid type linear administration vector has been grafted.

In this invention, the terms:

"capable of hybridising" or "hybridisation" are used to mean the formation of hydrogen links, also known as a Watson-Crick match between complementary bases, usually on two strands of nucleic acid to form a double helix duplex, or triplex if the oligonucleotide consists of a double strand.

The degree of complementarity between two sequences of nucleic acid with identical length is determined by comparing the first sequence after alignment with the sequence complementary to the second sequence. The degree of complementarity is calculated by determining the number of identical positions for which the nucleotide is identical between the two sequences thus compared, by dividing this number of identical positions by the total number of positions, and multiplying the result obtained by 100 to obtain the degree of complementarity between these two sequences.

"gene coding for PKC", means the genomic sequence of PKC comprising the introns and exons of this gene.

"PKC beta-1", means the beta-1 isoform of the PKC

"product of genes coding for PKC", means messenger RNA sequences.

The oligonucleotide according to the invention preferably hybridises specifically with the gene or products of the gene coding for PKC beta-1 isoform. In particular, the oligonucleotide according to the invention is capable of hybridising with the DNA of the gene that is coding for PKC and/or with mRNA deriving from these genes. Oligonucleotides according to the invention comprise sufficiently identical nucleotides to hybridise specifically. This property is usually called "antisense".

In this invention, the term "specific hybridisation" means in particular that there is a sufficient degree of complementarity to avoid non-specific fixation of the oligonucleotide on a non-targeted sequence under conditions in which specific fixation is required. It is understood that the oligonucleotide does not need to have a 100% complementarity with the target nucleic acid sequence to hybridise specifically. In particular, an oligonucleotide with a degree of complementarity equal to at least about 80% is capable of specifically hybridising with the nucleic acid chosen as the target.

The activation role of tyrosinase by phosphorylation played by PKC and the key role of tyrosinase in melanogenesis are known. The use of an oligonucleotide directed against a messenger RNA coding for an enzyme or for a protein and even beta-1 PKC in order to modulate the expression is also known.

However, the role of beta-1 isoform of Protein Kinase C was not known specifically in the melanogenesis. The ubiquitous nature of PKC means that the non-specificity of the action of conventional inhibitors is unacceptable for dermatological or pharmaceutical use. Furthermore, conventional inhibitors of PKC beta cover the beta-1 and beta-2 isoforms and therefore are not specific to melanocytes since cells such as Langerhans cells present in the skin have a PKC beta-2 activity.

The technique produced by the inventors of this invention is the only technique that can be used to obtain a specific action on the beta-1 isoform by preserving other isoforms of PKC beta and PKC in general. Furthermore, this technique had never been used as a means of depigmentation.

The oligonucleotide according to the invention is determined so that it will hybridise directly to the messenger RNA or the gene. They thus enable an ultimate modulation of the quantity of PKC beta-1 produced by the genes.

In one preferred embodiment, the oligonucleotide according to the invention is capable of non-specifically hybridising with any one of regions 5' to 3' that is or is not coding for the genes coding for PKC beta-1.

In one more preferred embodiment, the oligonucleotide sequence is one of the sequences SEQ ID No. 1 to SEQ ID No. 5 with the following meaning:

```
SEQ ID No. 1:    ACACCCCAGGCTCAACGATG
SED ID No. 2:    TGG ACT TTG CAT TCA CCT AC
SEQ ID No. 3:    AAA CCC CTC TAA GAC AAG CT
SED ID No. 4:    GCC ACC ATC TCC ACC GTG AA
SED ID No. 5:    CCG AAG CTT ACT CAC AAT TT
```

In one even more preferred embodiment, the sequence is one of the sequences SEQ ID No. 1 and SEQ ID No. 4, and more particularly sequence SEQ ID No. 1.

In another preferred embodiment according to the invention, the oligonucleotide comprises one or several chemical modifications in its sugar parts, its nucleobase parts or its internucleotide skeleton that confer improved physicochemical characteristics on the said oligonucleotide.

"Improved physicochemical characteristics" means desirable characteristics of the oligonucleotide according to the invention such as increased bioavailability, increased affinity for target sequences, increase in cellular internalisation or better biological stability or an increase in the stability in the presence of cellular nucleases.

For example, some modifications that can confer these characteristics are 2'-O-alkyl and 2'-O-fluoro derivatives on the sugar part of the nucleoside, and phosphorothioate derivatives or methylphosphonate derivatives at the internucleotide skeleton.

In one preferred embodiment according to the invention, the oligonucleotide is chemically modified in that:
- a part of the phosphodiester groups in its internucleotide skeleton is replaced by phosphorothioate groups.
- a part of the phosphodiester groups of its internucleotide skeleton is replaced by methylphosphonate groups.
- all phosphodiester groups are replaced by phosphorothioate groups.
- all phosphodiester groups are replaced methylphosphonate groups.
- phosphodiester groups are wholly or partly replaced by phosphorothioate groups and/or by methylphosphonate groups.
- a linear nucleic acid or peptidic acid type administration vector, or a circular plasmidic type administration vector, has been grafted onto the oligonucleotide.

Another purpose of this invention is a cosmetic composition containing the oligonucleotide described above and a cosmetically acceptable medium.

Such a composition may also contain one or several active agents to reinforce the required effects.

The said active agents that can be used in association with the oligonucleotide according to the invention, used pure or originating from extracts containing these molecules, are particularly the following compounds: an antisense oligonucleotide directed against tyrosinase gene expression products, an antisense oligonucleotide directed against tyrosinase-related-protein 1 (TRP-1) gene expression products, ellagic acid and its derivatives; hydroquinone; arbutin; resorcinol and its derivatives; vitamin C and its derivatives; pantothenate sulfonate and its derivatives; kojic acid; placentary extracts; molecules directly or indirectly interfering with the alpha-melanocyte stimulating hormone ($\alpha$-MSH) or its receptor or the adrenocorticotropic hormone (ACTH); polyols such as glycerine, glycol or propylene glycol; vitamins; keratolytic and/or desquamating agents such as salicylic acid and its derivatives; alpha-hydroxyacids such as lactic acid or malic acid, alone or grafted; ascorbic acid and its derivatives; retinoids and carotenoids in liposomic preparation or not, such as retinaldehyde; retinol and its derivatives such as palmitate, propionate or acetate, beta-carotene, antiglycation agents and/or antioxidants taken alone or in association such as tocopherol and its derivatives, ergothioneine, thiotaurine, hypotaurine, aminoguanidine, thiamine pyrophosphate, pyridoxamine, lysine, histidine, arginine, phenylalanine, pyridoxine, adenosine triphosphate; anti-inflammatory agents such as stearyl glycyrrhetinate; tranquillising agents and mixes of them, chemical or physical solar filters such as octyl methoxycinnamate, butyl-methoxydibenzoyl-methane, titanium oxide and zinc oxide; and deoxyribonucleic and/or nucleic acids.

In case of incompatibility, these active agents and/or these oligonucleotides can be incorporated in spherules, particularly vesicles formed from ionic or non-ionic amphiphilic lipids as described in French patent FR 2534487 and/or nanoparticles and/or nanospheres.

The cosmetic composition according to the invention is appropriate for topical use and therefore contains a cosmetically acceptable medium, in other words compatible with the skin.

The oligonucleotide sequence according to the invention may preferably be present in quantities varying from 0.00001% to 10%, and even better from 0.0003% to 3% of the total weight of the cosmetic composition.

The composition according to the invention may be in any normally used galenic form for topical application particularly in the form of an aqueous, hydroalcoholic or oily solution, an oil-in-water or water-in-oil or multiple emulsion, an aqueous or oily gel, a liquid, paste or solid anhydrous product, an oil dispersion in a polymeric phase such as nanospheres and nanocapsules or even better ionic and/or non-ionic type lipidic vesicles like those described in French patent FR 2534487.

This composition may be more or less fluid and may be in the form of a white or coloured cream, a pomade, a milk, a lotion, a serum, a paste or a foam. It may even be applied on the skin in the form of an aerosol. It may also be in powder or other solid form, for example in stick form. It may also be in the form of patches, pencils, brushes or applicators used for local application on spots on the face or hands. It may be used as a care product and/or as makeup.

In a known manner, the composition according to the invention may also contain additives normally used in the cosmetic field, such as hydrophilic or lipophilic gels, hydrophilic or lipophilic active constituents, preservation agents, antioxidants, solvents, odorants, fillers, filters, pigments, odour absorbers and colouring material. The quantities of these different additives are as conventionally used in the fields considered. Depending on the nature, these additives may be added in the fatty phase, in the aqueous phase, in lipidic vesicles and/or in nanoparticles.

In one preferred embodiment of the invention, the cosmetological composition is in the form of an emulsion containing an oil, an emulsifier chosen from among fatty acid and polyethylene glycol esters such as PEG-20 stearate, and fatty acid and glycerine esters such as glycerine stearate, and a co-emulsifier.

When the cosmetic composition of the invention is an emulsion, the proportion of the fatty phase can vary from 5 to 80% by weight, and preferably from 5 to 50% by weight with reference to the total weight of the composition. The oils, emulsifiers and co-emulsifiers used in the composition in emulsion form are chosen from among those conventionally used in the field considered. The emulsifying agent and the co-emulsifying agent are present in the composition in a proportion varying from 0.3% to 30% by weight, and preferably from 0.5% to 20% by weight compared with the total weight of the composition.

Oils that can be used in association with oligonucleotides according to the invention include mineral oils (Vaseline oil), vegetable origin oils (avocado oil, Soya oil), animal origin oils (lanoline), synthetic oils (perhydrosqualene), silicone oils (cyclomethicone) and fluorine oils (perfluoropolyethers). Fatty alcohols (cetylic alcohol), fatty acids, waxes (Carnauba wax, ozokerite) can also be used as fatty materials.

For example, emulsifiers and coemulsifiers that can be used in association with oligonucleotides according to the invention include fatty acid and polyethylene glycol esters such as PEG-20 stearate and fatty acid and glycerine esters such as glyceryl stearate.

Hydrophilic gelifiers that can be used in association with oligonucleotides according to the invention include in particular carboxyvinylic polymers (carbomer), acrylic copolymers such as acrylate/alkylacrylate copolymers, polyacrylamides, polysaccharides, natural gums and clays. Lipophilic gelifiers include modified clays like bentones, metallic salts of fatty acids, hydrophobic silica and polyethylenes.

Another purpose of this invention is the use of an oligonucleotide sequence directed against transcription products of genes coding for PKC beta-1 for fabrication of a cosmetic composition.

This cosmetic composition is useful to depigment and/or bleach the human skin and/or hair.

Another purpose of this invention is the use of at least one oligonucleotide as an active constituent inhibiting synthesis of melanin for fabrication of a topical pharmaceutical composition designed for the treatment or prevention of regional hyper pigmentation by melanocyte hyper-activity such as idiopathic melasma, local hyper pigmentation due to hyperactivity and benign melanocyte proliferation such as pigmentary age spots (actinic lentigos), accidental hyper pigmentation such as photosensitization or post-lesion healing, and for the treatment of some leucodermias such as vitiligo.

In one preferred embodiment according to the invention, use is characterised in that the oligonucleotide(s) according to the invention represent(s) 0.00001% to 10%, preferably 0.0003% to 3% of the total weight of the said topical pharmaceutical composition.

The pharmaceutical composition will be administered simultaneously, separately or over a period of time in association with one or several active agents.

The following examples present the invention, but are not limitative.

For stability reasons in in-vitro culture media and in accordance with standard practice, examples 2 to 4 were made with phosphorothioate derivatives and examples 5 to 12 were made indifferently with phosphorothioate or phosphodiester derivatives.

All percentages in the following examples are given by weight unless mentioned otherwise.

EXAMPLE 1

Synthesis of Oligonucleotides

Oligonucleotides were synthesized with an automatic synthesiser (Perseptive Biosystems Expedite model 8909) using standard chemistry of phosphoramidite derivatives using the manufacturer protocols. The β-cyanoethyldiisopropylphosphoramidites were supplied by the Perseptive Biosystems company. For the phosphodiester oligonucleotides, the phosphite oxidation step was carried out with an iodine solution. Concerning phosphorothioate oligonucleotides, the phosphite oxidation step was carried out using a 0.05 M solution of 3H-1,2-benzodithiol-3-one 1,1-dioxide in anhydrous acetonitrile. After cleavage of the column (Controlled Pore Glass, Perseptive Biosystems) and total deprotection of the sequence by 18 h treatment at 55° C. by a 33% ammonia solution, the oligonucleotides were purified by precipitation in ethanol in the presence of sodium acetate. High-pressure liquid chromatography inspections were then made by ion exchanging chromatography with elution by a gradient of sodium chloride and by chromatography in C18 reverse phase with elution by a gradient of acetonitrile in the presence of triethylammonium acetate.

For example, the following oligonucleotides were synthesised. They are described in Table 1. There are five sequences in this table, numbered SEQ ID No. 1, SEQ ID No. 2, SEQ ID No. 3, SEQ ID No. 4 and SEQ ID No. 5. Studies were carried out on their depigmenting activity as reported in the following examples and more specifically for sequence SEQ ID No. 1.

The numbers mentioned in table 1 under each end of the sequences indicate the position of the oligonucleotide in the original sequences.

The sequence originates from the so-called <<HSPB1A>> sequence of the messenger RNA coding for beta 1 type protein kinase C (Genbank accession number X06318).

An oligonucleotide based on SEQ ID No. 1 according to the invention was also synthesised, namely a <<sense control>> sequence referred to as SEQ ID No. 6 in table 1, consisting of reversing the order of bases in sequence SEQ ID No. 1, for comparison purposes and to confirm the specific nature of oligonucleotides according to the invention with regard to genes or products of genes coding for PKC beta 1.

TABLE 1

| SEQ ID NO. | OLIGONUCLEOTIDE SEQUENCE | LOCUS |
|---|---|---|
| 1. | ACA CCC CAG GCT CAACGA TG<br>2186                      2167 | HSPKCB1A |
| 2. | TGG AGT TTG CAT TCA CCT AC<br>2168                      2149 | HSPKCB1A |
| 3. | AAA GGC CTCTAA GAC AAG CT<br>2285                      2266 | HSPKCB1A |
| 4. | GCC AGC ATCTGC ACC GTG AA<br>2250                      2231 | HSPKCB1A |
| 5. | CCC AAG CTTACT CAC AAT TT<br>2569                      2250 | HSPKCB1A |
| 6. | GTA GCA ACTCGG ACC CCA CA<br>2167                      2186 | HSPKCB1A |

EXAMPLE 2

Anti-PKC Beta 1 Activity of Sequence SEQ ID No. 1 on Melanocytes by Western-Blot M4Beu melanocytes are isolated cells of human melanoma (R Jacubovich and J. F. Dore Cancer Immunol.), Immunother., 7 (1979), 59-64.).

The culture medium used for these cells is the Dubelco's Modified Eagle medium supplemented with 10% of foetal calf serum (Gibco, Paisley, GB) and gentamicine at a concentration of 4 µg/ml.

M4Beu cells are seeded with 500 000 cells per box using SEQ ID No. 1 or SEQ ID No. 6 at 1 µM in the medium, and the medium is replaced once with SEQ ID No. 1 or SEQ ID No. 6 for 3 days, until confluence of the cells, the cells being recovered 24 hours after the last treatment.

When the cells are confluent, the culture medium is eliminated and cells are rinsed twice with PBS. The cells are then collected by scraping into 200 µl of complete lyse buffer. The suspension is frozen at −80° C. The cellular lysate is obtained by sonication at an amplitude of 7 µm for 2×10 s.

The cellular lysate proteins are analysed using the Bradford calorimetric method and using the Biorad kit micro method (Reference: Bio-Rad protein assay 500-0002, Hercules Calif., USA).

Electrophoresis of proteins is done in a 1 mm thick polyacrylamide minigel with 7.5% under denaturing and reducing conditions, in discontinuous buffer according to the Laemmli method (1970). Gels with 7.5% T, 2.7% C are used to separate proteins with a molecular mass of 30 to 200 kDa, which enables migration of PKCB to the middle of the gel.

15 µg of the cellular lysate protein is deposited with 15 or 20 µl of lyse buffer to deposit a fixed volume. 4 or 5 µl of 4× migration blue is added to the lysates that are then heated to 95% for 5 minutes to denature the proteins.

Electrophoresis is performed under refrigeration at constant amperage and non-limiting voltage.

After electrophoresis, the gel is washed in the transfer buffer for renaturation of proteins. A PVDF (polyvinylidenedifuoride) membrane with good mechanical strength and high protein fixation capacity is also balanced in the same transfer buffer.

The transfer is made by electroelution of proteins outside the gel on the PVDF membrane. The instrument, the Transblot SD (semi-dry cell), makes the transfer in a horizontal configuration. In order to neutralise specific sites, the membrane is placed in semi-skimmed powder milk (Régilait®) dissolved in the TBS-T buffer.

The membranes are washed and then incubated with the primary antibody, in other words beta I or beta II anti-PKC, while stirring for one hour at ambient temperature.

The primary antibody is a beta I anti-PKC rabbit or beta II human polyclonal antibody. It is used at 0.02 µg/ml (Santacruz Biotechnology, Santa Cruz, Calif., USA). In order to eliminate excess primary antibody, the membranes are rinsed with TBS-T and then incubated with the secondary antibody for one hour at ambient temperature. The secondary antibody is an anti-rabbit taken from a monkey coupled with horseradish peroxydase (Amersham, Buckinghamshire, GB). The excess antibody is eliminated by successive rinsing operations in TBS-T.

Proteins are detected by chemoluminescence using luminol as the substrate for peroxydase (ECL kit, Amersham, Buckinghamshire, GB). After incubation of the membrane with luminol and an amplifier, the membrane is covered with an autoradiographic film (Hyperfilm ECL, Amersham, Buckinghamshire, GB). The film exposure time on the membrane is 30 minutes. The spots obtained are quantified using the "Biolise 3.02V" software (BMG LABTECH GmbH, Hanns-Martin-Schleyer-Str. 10, D-77656 Offenburg/Germany). This software calculates the volume of spots.

These volumes are used to calculate a percent inhibition with respect to an experimental control as follows: [1-(sample volume/control volume)]×100. The results are given in Table 2 below.

TABLE 2

| | Percent inhibition of PKC-beta 1 |
|---|---|
| control | 0 |
| SEQ ID No. 6 | 5 |
| SEQ ID No. 1 | 100 |

EXAMPLE 3

Anti-PKC Beta-1 Activity of Sequence SEQ ID No. 1 on Melanocytes by RT-PCR.

M4Beu melanocytes are isolated cells of human melanoma (R Jacubovich and J. F. Dore Cancer Immunol. Immunother., 7 (1979), 59-64.).

The culture medium used for these cells is Dubelco's Modified Eagle medium supplemented with 10% of foetal calf serum (Gibco, Paisley, GB) and gentamicine at a concentration of 4 µg/ml.

M4Beu cells are seeded with 500 000 cells per box with SEQ ID No. 1 or SEQ ID No. 6 at 1 µM in the medium and for 3 days the medium is changed once with SEQ ID No. 1 or SEQ ID No. 6 until confluence of the cells, the cells being recovered 24 hours after the last treatment.

The culture medium is then eliminated. The cell lawn is rinsed with PBS. The cells are incubated for 1 minute with a solution of trypsine-EDTA, the reaction is stopped by the addition of the medium supplemented with 10% of SVF. The cell suspension obtained is transferred into a 15 ml tube and centrifuged to obtain the celiular residue. This residue is then rinsed twice with PBS. It may be frozen dry at −80° C.

The total RNA will be isolated from these residues. After checking that β-mercaptoethanol has been added to the SV RNA lyse buffer, 175 µl of this buffer is added to the cellular residue. Cellular extracts are diluted in a solution of SDS (Sodium Dodecyl Sulphate) containing a large concentration of guanidine thiocyanate (SV RNA lyse buffer) to destroy the nucleoproteic complexes associated with the RNAs and thus gives a selected precipitation of cellular proteins, while the RNA remains in solution. After centrifuging to remove the precipitated proteins and cell debris from the lysate, the RNA will be purified from this residue. The clear lysate solution is thus recovered in a clean tube.

The RNA is selectively precipitated by an ethanol solution. This precipitation is transferred onto the column where the RNA will bond to glass fibres. After washing of the column with the SV RNA washing solution, the RNAs remain fixed to the column.

The RNase-free DNase I is applied directly to the column to digest contaminating genomic DNA. The DNase is stirred for 15 minutes, the reaction is stopped by the addition of 200 µl of Stop SV DNase solution on the column.

Then after washing with the RNA SV washing solution, the total RNAs are finally eluted from the column by the addition of 100 µl of nuclease-free water.

RNAs are dosed at 260 nm. One optical density unit corresponds to 40 µg/ml of RNA. The absorbance ratio at 260 nm and at 280 nm (DO 260/DO 280) provides information about the purity of the prepared RNA and must be between 1.8 and 2, the presence of proteins may reduce this ratio.

The concentration (µg/ml)=DO at 260 nm×40× reading dilution factor.

Non-degradation of RNAs is verified by electrophoresis of an aliquot of 2 µg of agarose minigel at 0.8%. RNAs are displayed using TBE.

The gel is prepared by dissolving 0.4 g of agarose in 50 ml of tris borate buffer, TBE 1×, by heating. 2.5 µl of BET at 10 mg/ml is added at the time of pouring the gel.

Migration is done at 80V for 30 minutes.

18 s, 28 s and 4 s RNAs are coloured with BET and displayed under UV (Table Bioblock Scientific, Illkirch, France, wavelength 312 nm).

Non-degraded samples show 2 intense bands of 28 s and 18 s RNA, and a less intense band of 4 s RNA.

Two tubes are prepared for each extracted RNA: one tube in which the enzyme (Reverse Transcription (RT) M-MLV, Gibco, Paisley, GB) will be added (RT+), and one tube in which the enzyme will not be added (RT−). The enzyme is capable of synthesizing a complementary strand starting from a single strand of RNA in the presence of seeds.

The results are given in Table 3.

TABLE 3

|  | RT+ | RT− |
| --- | --- | --- |
| pdN(6) 6 U/ml 0.3 U in the test | 1 µl | 1 µl |
| total RNA 2 µg/µl in the test | 2 µg/ul | 2 µg/µl |
| H2O | to make 11.5 µl | to make 11.5 µl |

In Table 3, each pdN(6) is an oligonucleotide composed of 6 nucleotides at random, and will be used as a seed for reverse transcriptase.

These tubes are heated to 65° C. for 5 minutes to denature the RNAs.

During this time, the mix described in table 4 below is prepared for each RT+ and RT− tube.

TABLE 4

| MIX | ×1 tube |
| --- | --- |
| RT 5× buffer 1× in the test | 4 µl |
| dNTP (10 mM) 500 µM in the test | 1 µl |
| dTT (0.1M) 10 mM in the test | 2 µl |
| RNA guard | 0.5 µl |
| TOTAL | 7.5 µl |

7.5 µl of the mix is added into each RT+ and RT− tube.

1 µl of RT enzyme (200 U in the test) is then added into the RT+ tubes, while 1 µl of water is added into the RT− tubes. Then all the tubes are incubated for 1 hour at 42° C., which is the optimum temperature for the enzyme to be most effective. The reaction is then stopped by incubating the tubes at 95° C. for 5 minutes.

Thus there is DNA in the RT+ tubes since the RT has synthesised the complementary strand of all RNAs. However there is no DNA in the RT− tubes, since there was no enzyme. The RT− tubes are used as a control in the PCR reaction, to determine whether or not there was contamination by genomic DNA.

A PCR, in other words an enzymatic amplification of DNA, is made for each RT+ and RT− tube.

Two pairs of primers act as a seed for the enzyme (Eurobiotaq® DNA polymerase, Eurobio): pair 1=primer PKCβI/Act1, pair 2=primer PKCβ/Act2. Therefore, there will be amplification of PKCβ or βI and actine in the same tube. Actine is used in this case as an internal control.

The following solutions were prepared for each DNA originating either from the Reverse Transcriptase (RT+) or Non-Reverse Transcriptase (RT−) reaction:

| RT DNA 100 ng in the test | MgCl2 (50 mM) 2 mM in the test | H2O | Total |
| --- | --- | --- | --- |
| 1 µl | 2 µl | 12 µl | 15 µl |

The following mix presented in Table 5 is prepared for all tubes.

The final reaction volume is 50 µl.

The reaction takes place in a PCR instrument (Crocodile II, Appligene, Illkirch, France).

The reaction conditions are as follows for pair 1:

1 DNA denaturation cycle (opening of the 2 strands): 5 minutes at 95° C.

40 DNA amplification cycles: 30 seconds at 95° C. (opening of strands)

30 seconds at 56° C. (specific fixation of seeds 30 seconds at 72° C. (elongation of new strands)

1 newly formed DNA elongation cycles: 7 minutes at 72° C.

TABLE 5

| Mix PCR | ×1 tube |
| --- | --- |
| PCR 10× buffer 1× in the test | 5 µl |
| dNTP (10 mM) 500 mM in the test | 1 µl |
| Sense actine primer (5 µM) 0.05 µM in the test | 0.5 µl |
| Antisense actine primer (5 µM) 0.05 µM in the test | 0.5 µl |
| PKCβ or PKCβI sense primer (5 µM) 1 µM in the test | 1 µl |
| PKCβ or PKCβI antisense primer (5 µM) 1 µM in the test | 1 µl |
| H2O | 25.8 µl |
| Taq | 0.2 µl |
| Total | 35 µl |

The reaction conditions are as follows for pair 2; the reaction cycles are the same but the specific seed fixation temperature is 50° C.

Quantification of the expression of PKCβ or βI RNA with respect to the expression of actine.

DNA fragments are deposited on a 2% agarose gel coloured in TBE. Electrophoretic migration is done at 80V for 45 minutes. The bands corresponding to RNA are displayed under UV (312 nm UV Table, Bioblock scientific, Illkirch, France). Two bands appear with DNAs with RT+ tubes and none in RT− tubes. A molecular weight scale is deposited at the same time to determine the size of the bands obtained.

For pair 1, the fragment corresponding to PKCβI RNA is 547 pb while the fragment of RNA corresponding to the actine is 308 pb.

For pair 2, the fragment corresponding to PKCB RNA is 380 pb while the fragment of RNA corresponding to the actine is 514 pb.

The bands obtained are quantified using the "Biolise 3.02V" software. This software is capable of calculating the volume of the bands.

We compare the PKCβ/actine or PKCβI/actine band volume ratio.

Table 6 contains the results.

TABLE 6

| | Percentage of expression of mRNA coding for PKC-beta 1 |
|---|---|
| SEQ ID No. 6 | 0 |
| SEQ ID No. 1 | 55 |

EXAMPLE 4

Anti-Tyrosinase Activity of SEQ ID No. 1 on Melanocytes

M4Beu melanocytes are isolated cells of human melanoma. (R Jacubovich and J. F. Dore Cancer Immunol. Immunother., 7 (1979), 59-64.).

The culture medium used for these cells is Dubelco's Modified Eagle Medium supplemented with 10% of fœtal veal serum (Gibco, Paisley, GB) and gentamicine at a concentration of 4 µg/ml.

The M4Beu cells are seeded with 100 000 cells per box using SEQ ID No. 1 or SEQ ID No. 6 at 1 µM in the medium and the medium is replaced once with SEQ ID No. 1 or SEQ ID No. 6 for 3 days until confluence of the cells, the cells being recovered 24 hours after the last treatment.

After 3 washings of the boxes with physiological serum; a plastic scraper is used to recover the cells in 10 µl of buffer (0.0625 M Tris HCl pH6, SDS 3%, Glycerol 10%). One electrophoresis (Ready gel Tris-glycine 7.5% (Biorad, Hercules, Calif., USA, ref 161-09000) 1×SDS Tris-glycine migration buffer (Biorad, Hercules, Calif., USA, ref: 161-0732) is made with a cellular lysate deposition with a quantity of 30 µg of protein per well.

After migration at 15 mA, the gel is unmoulded and is rinsed for 20 minutes in PBS 3 times while stirring gently to bring the pH to 7.5 (optimum pH for the tyrosinase activity).

The tyrosinase activity is revealed by incubation of the gel for 3 hours at 37° C. in 10 ml of a solution (1 g/l PBS of MBTH Sigma M8006, 1 g/l of PBS of DOPA Sigma D9628). The gel is rinsed 3 times in PBS to stop the tyrosine reaction on its substrate. After taking a photograph, the quantification is then done with the "Biolise 3.02V" software.

Table 7 contains the results.

TABLE 7

| | Percent inhibition of the tyrosinase activity |
|---|---|
| SEQ ID No. 6 | 0 |
| SEQ ID No. 1 | 55 |

EXAMPLE 5

Powder for Lightening the Face Colour

A powder was prepared with the composition presented in Table 8

TABLE 8

| Microcellulose | 20.00% |
|---|---|
| Sodium lauryl sulfoacetate | 15.00% |
| Oligonucleotide SEQ ID NO. 1 | 1.00% |
| Odorant, colouring agents, preservation agents | as needed |
| Talc | to make 100% |

This powder performs two actions. It cleanses the skin and it also lightens the colour, when used regularly for several days. It can be applied onto the skin of the face once or twice a day.

EXAMPLE 6

Depigmenting Day Face Emulsion-Gel

An emulsion-gel was prepared with the composition presented in Table 8.

TABLE 9

| Glycerine | 5.00% |
|---|---|
| caprylic/capric/succinic triglycerides | 5.00% |
| Octyl methoxycinnamate | 1.00% |
| Copolyol dimethicone | 0.50% |
| Acrylates/C10-30 alkyl acrylate crosspolymer | 0.50% |
| Oligonucleotide SEQ ID No. 4 | 0.01% |
| Neutralising agent | as needed. |
| Preservation agents, odorant, colouring agents | as needed. |
| Water | to make. 100% |

Some persons subjected to more or less intense irradiation due to daylight, or even direct sunlight, would like to keep a light skin and avoid the appearance of pigmenting spots.

The use of the emulsion-gel defined above provides the means of achieving this purpose. This composition is usually applied on the face in the morning. It is equally effective for preventive and remedial action on regular or irregular pigmentation of the face.

EXAMPLE 7

SPF 30 Protective Fluid Preventing Pigmentation Spots

A protective fluid with the composition presented in Table 10 was prepared.

The protective fluid is used to prevent the appearance of pigmentation spots in persons subject to this phenomenon, before exposure to intense solar radiation. Note that the presence of a high concentration in the solar filter compensates for the reduction in natural protection due to the drop in the melanin content.

TABLE 10

| Volatile pentacyclomethicone | 49.00% |
|---|---|
| Titanium dioxide | 15.00% |
| Octyl methoxycinnamate | 7.50% |
| Glycerine | 5.00% |
| Phenyltrimethicone | 5.00% |

TABLE 10-continued

| | |
|---|---|
| Copolyol dimethicone | 3.00% |
| Polymethylmethacrylate | 2.50% |
| Butyl methoxydibenzoyle methane | 1.00% |
| Oligonucleotide SEQ ID NO. 1 | 0.1% |
| Neutralising agent, odorant, preservation agents, antioxydisers | as needed. |
| Water | to make 100% |

EXAMPLE 8

Depigmenting Face Cream

A cream was prepared with the composition presented in Table 11.

This cream can be used to treat irregular skin pigmentation, by attenuating or eliminating age spots or actinic pigmentation spots. It makes the skin colour uniform and lighter.

TABLE 11

| | |
|---|---|
| Glyceryl stearate + Peg-100 stearate | 5.00% |
| Hydrogenated polyisobutene | 4.00% |
| Magnesium ascorbyl phosphate | 3.30% |
| Glycerol tricaprylate/caprate | 3.00% |
| Squalane | 3.00% |
| Glycerine | 2.00% |
| Beeswax | 1.50% |
| Cetearyl octanoate | 1.50% |
| Cetylic alcohol | 1.00% |
| Stearylic alcohol | 1.00% |
| Dimethicone | 1.00% |
| Xanthane gum | 0.30% |
| Ethylene diamine tetracetic acid | 0.20% |
| Citric acid | 0.10% |
| Sodium citrate | 0.10% |
| Oligonucleotide SEQ ID No. 1 | 0.10% |
| Neutralising agent, Odorant, Preservation agents | as needed |
| Water | to make 100% |

EXAMPLE 9

Face Lotion to Lighten the Skin Colour

A lotion was prepared with the composition given in Table 12.

TABLE 12

| | |
|---|---|
| Ethyl alcohol | 30.00% |
| PPG-3 Myristyl ether | 5.00% |
| Glycerine | 2.00% |
| Carbomer | 0.20% |
| Polysorbate 20 | 0.20% |
| Oligonucleotide SEQ ID No. 1 | 0.01% |
| Neutralising agent, Odorant, Preservation agents | as needed |
| Water | to make 100% |

This lotion to lighten the skin colour is to be used after removal of makeup and after cleaning the skin.

EXAMPLE 10

Lightening Face Serum

A serum was prepared with the composition presented into Table 13.

TABLE 13

| | |
|---|---|
| Water | to make 100% |
| Glycerine | 2% |
| Tetrasodium EDTA | As necessary to required pH |
| Citric acid | |
| Trisodium citrate | |
| Xanthane gum | 0.25% |
| Polyacrylamide, C13.14 isoparaffin, laureth-7 | 0.5% |
| Dimethicone copolyol | 0.25% |
| Oligonucleotide SEQ ID No. 1 | 0.1% |
| Odorant, colouring agent, conservation agent | as needed |

A drop of this very concentrated composition of serum is applied on the face, usually before application of a face cream. This serum is usually used in one- or two-week cures to obtain or maintain a light colour.

EXAMPLE 11

Capillary Lotion to Lighten the Hair Colour

A capillary lotion was prepared with the composition presented in Table 14.

TABLE 14

| | |
|---|---|
| Water | to make 100% |
| Alcohol | 50% |
| Panthenylethyl ether | 0.5% |
| DL-α-tocopherol acetate | 0.2% |
| Polysorbate 60 | 1% |
| Oligonucleotide SEQ ID No. 1 | 0.01% |
| Odorant | 0.2% |
| Glycerine | 0.5% |
| Colouring agent | as needed |

This lotion is to be applied on the hair in the morning and the evening for as long as necessary to progressively lighten the hair colour. This duration is usually several weeks.

EXAMPLE 12

Anti-Spot Cream Gel for Hands

A gel cream was prepared with the composition presented in table 15.

This gel cream must be applied directly onto age spots (age lentigos) on the hands to attenuate colouring of the spots.

TABLE 15

| | |
|---|---|
| Caprilic/capric diglyceryl succinate | 6% |
| Octyl octanoate | 2.5% |
| Octyle methoxycinnamate | 6% |
| Oligonucleotide SEQ ID NO. 1 (phosphodiester) | 0.001% |
| Phenyltrimethicone | 2.5% |
| Benzophenon-3 | 0.5% |
| Sodium hyaluronate | 0.05% |
| Xanthane gum | 0.2% |
| Acrylates/C10.30 alkyl acrylate copolymer | 0.5% |
| Glycerine | 2% |

TABLE 15-continued

| | |
|---|---|
| PEG 150 | 3% |
| Neutralising agents, Colouring agents, odorant, preservation agents | as needed |
| Purified water | to make 100% |

EXAMPLE 13

Dermatological Solution to Treat Pathological Hyper Pigmentation

A serum is prepared with the composition given in Table 16.

TABLE 16

| | |
|---|---|
| Volatile pentacyclomethicone | 49.00% |
| Titanium dioxide | 15.00% |

TABLE 16-continued

| | |
|---|---|
| Octyl methoxycinnamate | 7.50% |
| Glycerine | 5.00% |
| Phenyltrimethicone | 5.00% |
| Copolyol dimethicone | 3.00% |
| Polymethylmethacrylate | 2.50% |
| Butyl methoxydibenzoylmethane | 1.00% |
| Oligonucleotide SEQ ID No. 1 | 2.00% |
| Neutralising agent, Odorant, Preservation agents, antioxidants | as needed |
| Water | to make 100% |

This serum is applied to the skin daily for the treatment of persons suffering from regional hyper pigmentation.

---

The invention claimed is:

1. A method of depigmenting or bleaching human skin, body hair or hair of a head of a subject to lighten a color for purely cosmetic purposes comprising topical application to the skin, the body hair or the hair of the head of said subject of a cosmetic composition comprising an oligonucleotide having SEQ ID NO. 4 and capable of specifically hybridising with genes or gene products coding for protein kinase C beta-1 (PKC beta-1) and modifying expression of only PKC beta-1, wherein the oligonucleotide is present in an amount of between 0.0003% and 3% of a total weight of the composition.

2. The method according to claim 1, wherein the oligonucleotide is capable of specifically hybridising with any 5' to 3' regions, coding or not coding for genes coding for PKC beta-1.

3. The method according to claim 1, wherein the oligonucleotide comprises one or more chemical modifications to its sugar moieties, its nucleobase moieties or its internucleotide skeleton, the aforesaid modifications conferring improved physicochemical characteristics to said oligonucleotide.

4. The method according to claim 1, wherein the oligonucleotide comprises a sugar moiety comprising a 2'-O-fluoro or 2'-O-alkyl substituent.

5. The method according to claim 1, wherein some phosphodiester groups of the oligonucleotide internucleotide skeleton are replaced by phosphorothioate groups.

6. The method according to claim 1, wherein some phosphodiester groups of the oligonucleotide internucleotide skeleton are replaced by methylphosphonate groups.

7. The method according to claim 1, wherein all phosphodiester groups of the oligonucleotide are replaced by phosphorothioate groups.

8. The method according to claim 1, wherein all phosphodiester groups of the oligonucleotide are replaced by methylphosphonate groups.

9. The method according to claim 1, wherein all phosphodiester groups of the oligonucleotide are replaced in whole or in part by phosphorothioate groups and/or by methylphosphonate groups.

10. The method according to claim 1, wherein the oligonucleotide is grafted to a linear nucleic acid or peptide vector, or a circular plasmid vector.

11. The method according to claim 1, wherein said composition comprises one or more active agents chosen from among an antisense oligonucleotide directed against tyrosinase gene expression products; an antisense oligonucleotide directed against tyrosinase-related-protein 1 (TRP-1) gene expression products; ellagic acid and its derivatives; resorcinol and its derivatives; vitamin C and its derivatives; pantothenate sulfonate and its derivatives; molecules interfering directly or indirectly with alpha-melanocyte stimulating hormone (a-MSH) or its receptor or with adrenocorticotropic hormone (ACTH); polyols such as glycerin, glycol or propylene glycol; vitamins; keratolytic and/or desquamating agents such as salicylic acid and its derivatives; alpha-hydroxyacids such as lactic acid or malic acid, alone or grafted; ascorbic acid and its derivatives; retinoids and carotenoids in liposomic preparation or not, such as retinaldehyde; retinol and its derivatives such as palmitate, propionate or acetate, beta-carotene; antiglycation agents and/or antioxidants alone or in association such as tocopherol and its derivatives, thiotaurine, hypotaurine, aminoguanidine, thiamine pyrophosphate, pyridoxamine, lysine, histidine, arginine, phenylalanine, pyridoxine, adenosine triphosphate; anti-inflammatory agents such as stearyl glycyrrhetinate; soothing agents and mixtures thereof; and chemical or physical sun blocks such as the octyl methoxycinnamate, butylmethoxydibenzoyl-methane, titanium oxide and zinc oxide.

12. The method according to claim 1, wherein said composition is presented in the form of an emulsion containing an oil, an emulsifying agent chosen from among fatty acid and polyethylene glycol esters such as PEG-20 stearate, and fatty acid and glycerin esters such as glycerin stearate, and an co-emulsifying agent.

13. A method for treatment of regional hyper-pigmentation by melanocyte hyperactivity such as idiopathic melasma, local hyper-pigmentation by benign melanocyte hyperactivity and proliferation such as pigmentary age spots (actinic lentigo), accidental hyper-pigmentation such as photosensitization or post-lesion healing in a subject in need thereof, comprising topical application to the hyper-pigmented skin areas of said subject of a topical pharmaceutical composition comprising an oligonucleotide having SEQ ID NO. 4 and capable of specifically hybridising with genes or gene products coding for protein kinase C beta-1 (PKC beta-1) and modifying expression of only PKC beta-1, wherein the oligonucleotide is present in an amount of between 0.0003% and 3% of a total weight of the composition.

14. The method of claim 1, wherein the topical application comprises application of the composition to the hair of the head.

15. The method of claim 1, wherein the topical application comprises application of the composition to the face.

16. The method of claim 1, wherein the application of the composition comprises application of a makeup.

17. The method of claim 1, wherein the composition comprises an SPF protective fluid.

18. The method of claim 1, wherein the composition further comprises at least one additional active agent that is a depigmenting substance.

19. The method of claim 18, wherein the active agent is selected from substances that inhibit the activity of tyrosinase, an antisense oligonucleotide directed against tyrosinase gene expression products, an antisense oligonucleotide directed against tyrosinase-related-protein 1 (TRP-1) gene expression products, hydroquinone and its derivatives, placentary extracts, kojic acid, arbutin, iminophenols, association of carnitin and quinone, amide derivatives of aminophenol, and derivatives of benzothiazole.

20. The method of claim 18, with the proviso that the topical application to the skin, the body hair and/or the hair of the head does not comprise skin having psoriasis or skin cancer.

* * * * *

UNITED STATES PATENT AND TRADEMARK OFFICE
CERTIFICATE OF CORRECTION

| | | |
|---|---|---|
| PATENT NO. | : 8,252,753 B2 | Page 1 of 1 |
| APPLICATION NO. | : 10/584982 | |
| DATED | : August 28, 2012 | |
| INVENTOR(S) | : Robin Kurfurst et al. | |

It is certified that error appears in the above-identified patent and that said Letters Patent is hereby corrected as shown below:

In the Specification, Column 5, line 14, please delete "SEQ ID No. 2: TGG ACT TTG CAT TCA CCT AC" and insert --SEQ ID No. 2: TGG AGT TTG CAT TCA CCT AC--.

Column 5, line 15, please delete "SEQ ID No. 3: AAA CCC CTC TAA GAC AAG CT" and insert --SEQ ID No. 3: AAA GGC CTC TAA GAC AAG CT--.

Column 5, line 16, please delete "SEQ ID No. 4: GCC ACC ATC TCC ACC GTG AA" and insert --SEQ ID No. 4: GCC AGC ATC TGC ACC GTG AA"--.

Signed and Sealed this
Eighth Day of January, 2013

David J. Kappos
*Director of the United States Patent and Trademark Office*